(12) United States Patent
Fu (10) Patent No.: US 9,848,842 B2
(45) Date of Patent: Dec. 26, 2017

(54) LATCHING MECHANISM FOR X-RAY TUBE ASSEMBLY AND X-RAY IMAGING SYSTEM

(71) Applicant: KONINKLIJKE PHILIPS N.V., Eindhoven (NL)

(72) Inventor: Yan Ning Fu, Suzhou (CN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 15/511,273

(22) PCT Filed: Sep. 25, 2015

(86) PCT No.: PCT/EP2015/072096
§ 371 (c)(1),
(2) Date: Mar. 15, 2017

(87) PCT Pub. No.: WO2016/046366
PCT Pub. Date: Mar. 31, 2016

(65) Prior Publication Data
US 2017/0281104 A1 Oct. 5, 2017

(30) Foreign Application Priority Data

Sep. 26, 2014 (WO) ................ PCT/CN2014/087505
Nov. 27, 2014 (EP) ..................................... 14195161

(51) Int. Cl.
| | |
|---|---|
| *A61B 6/00* | (2006.01) |
| *A61B 5/00* | (2006.01) |
| *A61B 6/02* | (2006.01) |
| *A61B 6/04* | (2006.01) |
| *A61B 6/12* | (2006.01) |

(52) U.S. Cl.
CPC .......... *A61B 6/4429* (2013.01); *A61B 5/0033* (2013.01); *A61B 6/02* (2013.01); *A61B 6/04* (2013.01); *A61B 6/12* (2013.01); *A61B 6/50* (2013.01)

(58) Field of Classification Search
CPC ............................... A61B 6/44; A61B 6/4429
See application file for complete search history.

(56) References Cited

U.S. PATENT DOCUMENTS

| | | |
|---|---|---|
| 3,229,090 A | 1/1966 | Eberline |
| 4,217,064 A | 8/1980 | Hogan |
| 4,511,275 A | 4/1985 | Span |

(Continued)

FOREIGN PATENT DOCUMENTS

| | | |
|---|---|---|
| EP | 0156112 A1 | 10/1985 |
| FR | 1396606 | 4/1965 |

(Continued)

*Primary Examiner* — Dani Fox (57) ABSTRACT

The present invention provides a latching mechanism for an x-ray tube assembly comprising a rotary plate, a first spring-loaded latch and a second spring-loaded latch which are disposed diametrically. The rotary plate comprises a first receiving portion and a second receiving portion spaced from each other by 90°. The first spring-loaded latch configured to be pressed removably into the first receiving portion to lock the x-ray tube assembly in a first position and the second spring-loaded latch is configured to be pressed removably into the second receiving portion to lock the x-ray tube assembly in a second position. According to the present invention, it is possible to make manufacturing tolerance control and assembly of the x-ray imaging system much simpler and easier.

13 Claims, 6 Drawing Sheets

(56) References Cited

U.S. PATENT DOCUMENTS

| | | |
|---|---|---|
| 4,759,048 A | 7/1988 | Ohlson |
| 5,997,176 A | 12/1999 | Fairleigh |
| 7,585,109 B2 | 9/2009 | Denley |

FOREIGN PATENT DOCUMENTS

| | | |
|---|---|---|
| GB | 838962 | 6/1960 |
| JP | 2008067770 A | 3/2008 |
| JP | 04392872 B2 | 1/2010 |

LATCHING MECHANISM FOR X-RAY TUBE ASSEMBLY AND X-RAY IMAGING SYSTEM

CROSS-REFERENCE TO PRIOR APPLICATIONS

This application is the U.S. National Phase application under 35 U.S.C. §371 of International Application No. PCT/EP2015/072096, filed on Sep. 25, 2015, which claims the benefit of CN Patent Application No. PCT/CN2014/087505, filed on Sep. 26, 2014 and EP Patent Application No. 14195161.6, filed on Nov. 27 2014. These applications are hereby incorporated by reference herein.

FIELD OF THE INVENTION

The invention relates to an x-ray imaging system in which an x-ray tube assembly may be rotated between a first position and a second position which is spaced from the first position by 90°, in particular to a latching mechanism for the x-ray tube assembly.

BACKGROUND OF THE INVENTION

As known, an x-ray imaging system at least comprises an x-ray tube assembly configured to generate and emit an x-ray and a detector configured to detect the x-ray that passes through a region of a subject, such as a human body, to be examined. The detector generates an electrical signal based on the detected X-ray and transfers the electrical signal to a processing unit to form an image of the region to be examined. When the region to be examined is imaged, a patient may need to maintain a standing posture. For another patient, it may be necessary to lie on his back when the region to be examined is imaged. Thus, the x-ray tube assembly should be capable of being rotated between a first position in which the x-ray is projected for example substantially vertically onto the region to be examined and a second position which is spaced from the first position by 90° about the rotating axis of the x-ray tube assembly and in which the x-ray is projected for example substantially horizontally onto the region to be examined.

Figure 1:
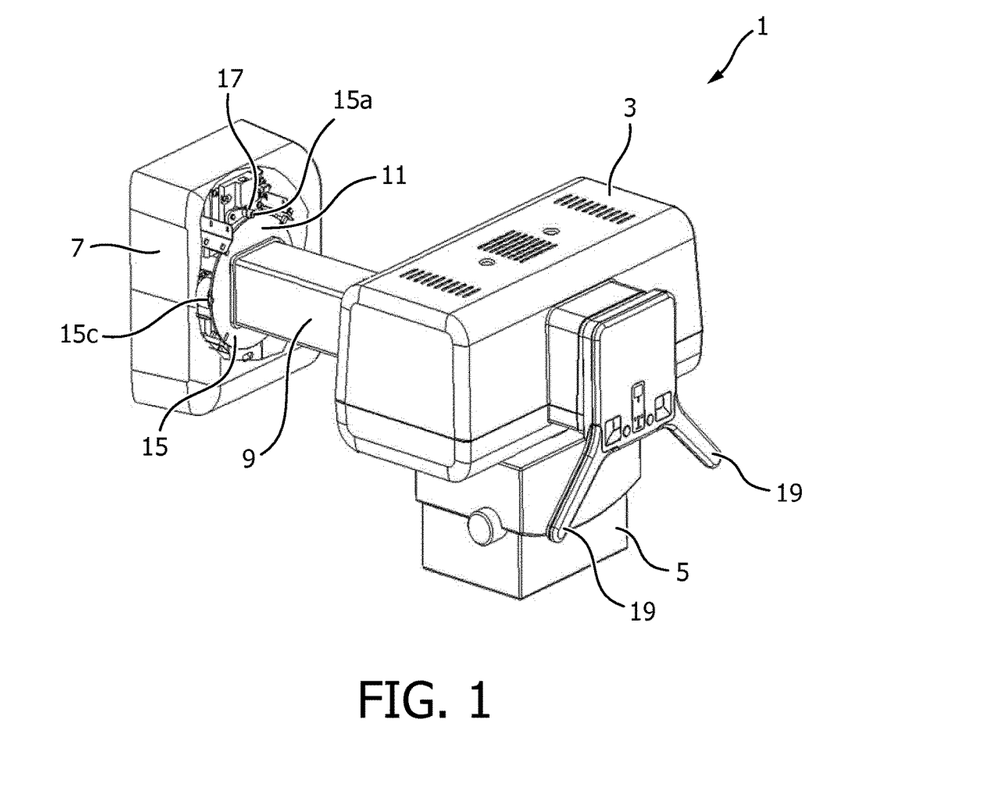
FIG. 1 shows a partial view of an x-ray tube assembly of a conventional x-ray imaging system.
Figures 2, 2A:
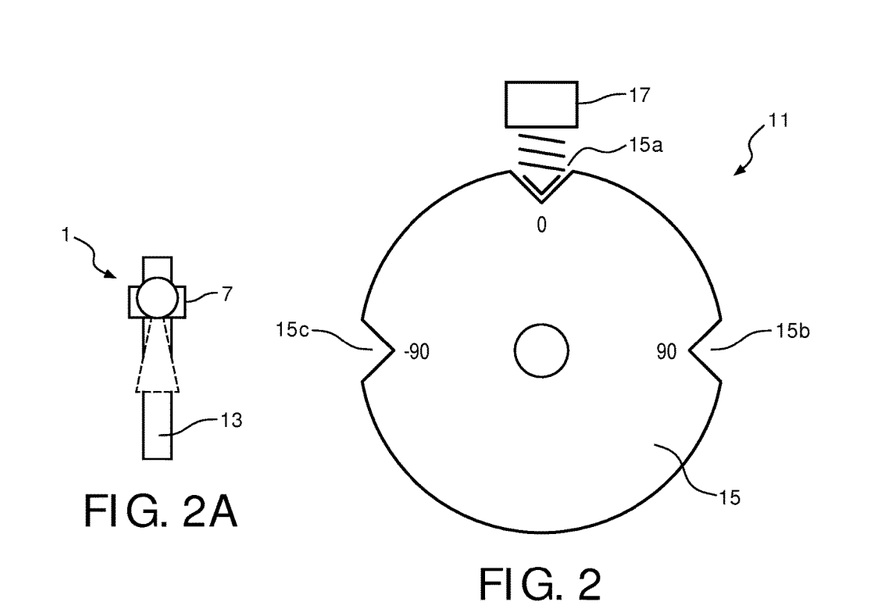
FIG. 2 is a schematic view showing a latching mechanism in which a rotary plate is locked in a first position.
FIG. 2A shows an orientation of an x-ray tube assembly corresponding to FIG. 2.
Figures 3, 3A:
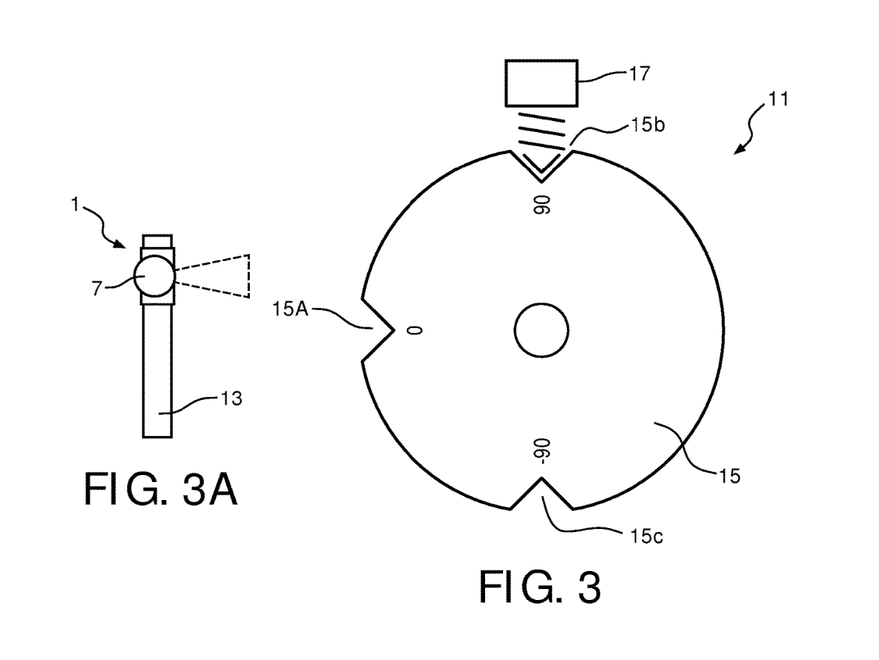
FIG. 3 is a schematic view showing a latching mechanism in which a rotary plate is locked in a second position.
FIG. 3A shows an orientation of an x-ray tube assembly corresponding to FIG. 3.

FIG. 1 shows a partial view of an x-ray tube assembly of a conventional x-ray imaging system. As shown in FIG. 1, the x-ray tube assembly 1 comprises an x-ray tube 3 configured to generate and emit an x-ray and a collimator 5 configured to collimate the x-ray generated by the x-ray tube 3 onto a region of a subject such as a human body to be examined. The x-ray tube assembly 1 is rotatably attached to a supporting part 7 through a tube arm 9 and a latching mechanism 11. The supporting part 7 is vertically movably mounted onto a tube column 13. FIG. 2 is a schematic view showing a latching mechanism in which a rotary plate is locked in the first position, FIG. 2A shows an orientation of an x-ray tube assembly corresponding to FIG. 2, FIG. 3 is a schematic view showing a latching mechanism in which a rotary plate is locked in the second position which is spaced from the first position by 90° about the rotating axis of the tube assembly 1, and FIG. 3A shows an orientation of an x-ray tube assembly corresponding to FIG. 3. As shown in FIGS. 2 and 3, the latching mechanism 11 comprises a rotary plate 15 to which the tube arm 9 is fixed and a spring-loaded latch 17. The rotary plate 15 is circular in shape and comprises a first notch 15a, a second notch 15b and a third notch 15c disposed on the periphery of the rotary plate 15. The second notch 15b and the third notch 15c are spaced from the first notch 15a by 90° and from each other by 180° about the rotating axis of the tube assembly 1. The spring-loaded latch 17 may be pressed removably into the first notch 15a to lock the x-ray tube assembly 1 in the first position in which the x-ray is projected substantially vertically onto the region to be examined. By grasping a handle 19 on the x-ray tube assembly 1 and rotating the x-ray tube assembly 1 to disengage the spring-loaded latch 17 from the first notch 15a against a force applied to the spring-loaded latch 17 by a spring, the rotary plate 15 is rotated so that the spring-loaded latch 17 may be pressed removably into one of the second notch 15b and the third notch 15c to lock the x-ray tube assembly 1 in the second position in which the x-ray is projected substantially horizontally onto the region to be examined. Of course, the spring-loaded latch 17 may lock the x-ray tube assembly 1 in a third position which is spaced from the first position by 90° and which is opposite to the second position when the rotary plate 15 is rotated in an opposite direction. Although the x-ray tube assembly 1 in the first position is aligned accurately to guarantee that the x-ray is projected substantially vertically onto the region to be examined, the x-ray is not always projected substantially horizontally onto the region to be examined when the x-ray tube assembly 1 is locked in the second position because of stack up of various tolerances such as manufacturing tolerances of tube arm, tube column, rail etc. Thus, more relevant parameters need to be carefully and repeatedly aligned, including the first position and/or the second position latching alignment during installation of the x-ray imaging system because the alignment of the first position latching and the second position latching are coupled with one another. This makes manufacturing tolerance control and installation of the x-ray imaging system much more complicated and difficult.

Thus, there is a need to make improvements on the conventional x-ray imaging system.

SUMMARY OF THE INVENTION

According to one aspect of the present invention, there is provided a latching mechanism for an x-ray tube assembly comprising:
  a rotary plate to which the x-ray tube assembly is fixedly mounted by means of a tube arm, the rotary plate being rotatably mounted to a supporting part to be rotatable about an axis relative to the supporting part, the axis passing through a point on the rotary plate perpendicularly to the rotary plate, the rotary plate comprising a first receiving portion and a second receiving portion, the second receiving portion being spaced from the first receiving portion by substantially 90° about the axis; and
  a first spring-loaded latch and a second spring-loaded latch which are fixed on the supporting part, the first spring-loaded latch and the second spring-loaded latch being disposed diametrically and adjacent the rotary plate, the first spring-loaded latch being configured to be pressed removably into the first receiving portion to lock the x-ray tube assembly in a first position, the second spring-loaded latch being configured to be pressed removably into the second receiving portion to lock the x-ray tube assembly in a second position which is spaced from the first position by substantially 90° about the axis in a first direction.

The skilled person would appreciate that the word "substantially" used together with a particular value (e.g. "substantially 90°") means the level of tolerance as well-known in the technical field. For example, the skilled person would appreciate that the level of tolerance is about +/−3 degrees for a particular angle value in some systems.

Additionally, all particular values specified throughout the text are meant to allow a certain level of tolerance in practical systems, as appreciated by the skilled person.

According to another aspect of the present invention, there is provided an x-ray imaging system comprising the aforementioned latching mechanism.

These and other objects, features and characteristics of the present invention, as well as the methods of operation and functions of the related structural elements and the combination of parts and economies of manufacture, will become more apparent upon consideration of the following description and the appended claims with reference to the accompanying drawings, all of which form part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF THE EXEMPLARY EMBODIMENTS

Figure 4:
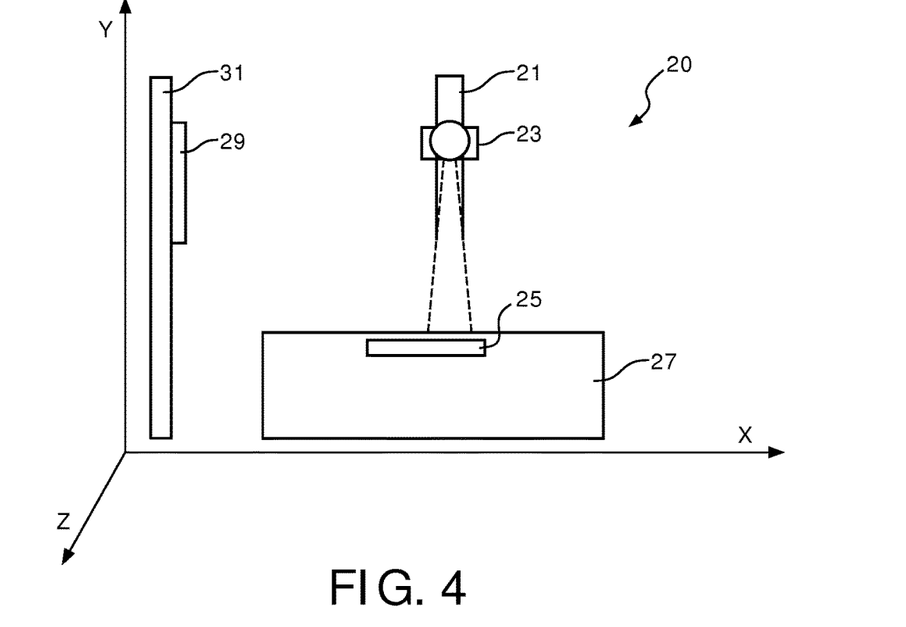
FIG. 4 is a schematic view of an x-ray imaging system in which an x-ray tube assembly is in the first position.
Figure 5:
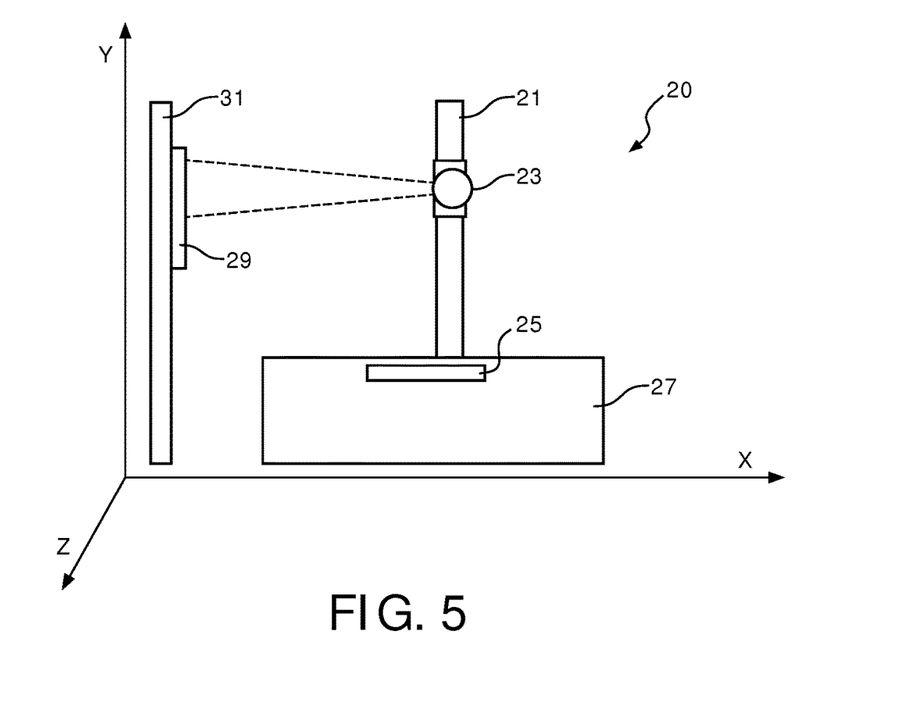
FIG. 5 is a schematic view of an x-ray imaging system in which an x-ray tube assembly is in the second position.

As shown in FIGS. 4 and 5, an x-ray imaging system 20 according to the present invention comprises a tube column 21 configured to move back and forth in an X-Y plane (for example on a rail), an x-ray tube assembly 23 being capable of moving vertically along the tube column 21, a first detector 25 mounted below a patient table 27, and a second detector 29 mounted on a wall stand 31. As well-known, the x-ray tube assembly 23 is rotatably attached to a supporting part by means of a tube arm (not shown) and a latching mechanism 33 so that the x-ray tube assembly 23 may be rotated between a first position and a second position which is spaced from the first position by 90° about the rotating axis of the x-ray tube assembly 23. The supporting part is mounted slidably to move vertically along the tube column 21. The first detector 25 is configured to detect an x-ray passing through a region of a subject such as a human body to be examined when the x-ray tube assembly 23 is locked in the first position and the patient lies on the patient table 27. The second detector 29 is configured to detect an x-ray passing through a region of the subject to be examined when the x-ray tube assembly 23 is locked in the second position and the patient stands in front of the wall stand 31.

Figure 6:
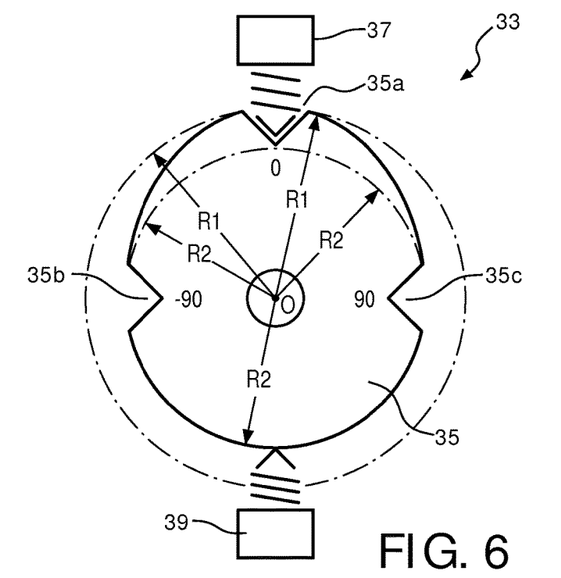
FIG. 6 is a schematic view showing a latching mechanism of a first embodiment of the present invention in which a rotary plate is locked in the first position.
Figure 6A:
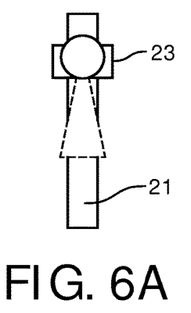
FIG. 6A shows an orientation of an x-ray tube assembly corresponding to FIG. 6.
Figure 7:
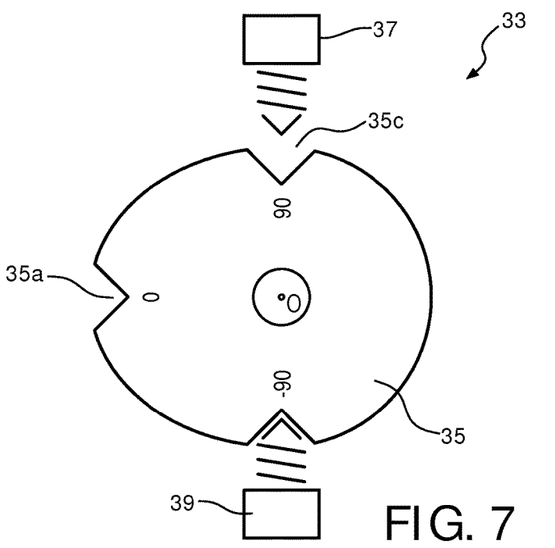
FIG. 7 is a schematic view showing a latching mechanism of a first embodiment of the present invention in which a rotary plate is locked in the second position.
Figure 7A:
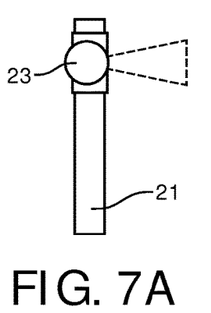
FIG. 7A shows an orientation of an x-ray tube assembly corresponding to FIG. 7.

FIG. 6 is a schematic view showing a latching mechanism of a first embodiment of the present invention in which a rotary plate is locked in the first position. FIG. 6A shows an orientation of an x-ray tube assembly corresponding to FIG. 6. FIG. 7 is a schematic view showing a latching mechanism of a first embodiment of the present invention in which a rotary plate is locked in the second position. FIG. 7A shows an orientation of an x-ray tube assembly corresponding to FIG. 7. As shown in FIGS. 6 and 7, the latching mechanism 33 of a first embodiment of the present invention comprises a rotary plate 35 to which the x-ray tube assembly 23 is fixedly mounted by means of a tube arm. The rotary plate 35 may be rotatably mounted to the supporting part so that the rotary plate 35 is rotatable about an axis relative to the supporting part. The axis passes through a point O on the rotary plate 35 perpendicularly to the rotary plate 35, and is also referred to as rotating axis hereinafter. The rotary plate 35 comprises a first notch 35a, a second notch 35b and a third notch 35c disposed on a periphery of the rotary plate 35. The second notch 35b and the third notch 35c are spaced from the first notch 35a by 90° and from each other by 180° about the rotating axis. The distance from point O to the first notch 35a is R1, the distance from the point O to the second notch 35b and the third notch 35c is R2, and R1>R2.

The latching mechanism 33 further comprises a first spring-loaded latch 37 and a second spring-loaded latch 39 which are fixed on the supporting part. The first spring-loaded latch 37 and the second spring-loaded latch 39 are disposed diametrically and adjacent the rotary plate 35. The first spring-loaded latch 37 is configured to be pressed removably into the first notch 35a to lock the x-ray tube assembly 23 in the first position in which the x-ray is projected substantially vertically onto the region to be examined, as shown in FIGS. 6 and 6A. The second spring-loaded latch 39 is configured to be pressed removably into the second notch 35b to lock the x-ray tube assembly 23 in the second position which is spaced from the first position by 90° about the rotating axis in an anticlockwise direction when the rotary plate 35 is rotated by 90° about the rotating axis in the anticlockwise direction, as shown in FIG. 7. In the second position, the x-ray is projected substantially horizontally onto the region to be examined, as shown in FIG. 7A. Furthermore, the second spring-loaded latch 39 is also configured to be pressed removably into the third notch 35c to lock the x-ray tube assembly 23 in the third position which is spaced from the first position by 90° in a clockwise direction when the rotary plate 35 is rotated by 90° in the clockwise direction about the rotating axis. In the third position, the x-ray is projected substantially horizontally onto the region to be examined in a direction opposite to the second direction.

The difference between R1 and R2 should be larger than a maximum distance over which the first spring-loaded latch 37 can move after the first spring-loaded latch 37 is removed out of the first notch 35a. In other words, this distance refers to a length over which the first spring-loaded latch 37 can stretch when the first spring-loaded latch 37 is removed out of the first notch 35a and transits into a state in which the first spring-loaded latch 37 has no contact with the rotary plate 35. Thus, only the second spring-loaded latch 39 is pressed removably into one of the second notch 35b and the third notch 35c, but the first spring-loaded latch 37 is not pressed into the other one of the second notch 35b and the third notch 35c when the x-ray tube assembly 23 is rotated by 90° about the rotating axis relative to the first position.

In the first embodiment, except for the locations where the first notch 35a, the second notch 35b and the third notch 35c are disposed, the rotary plate 35 may have an arc-shaped periphery. Thus, the rotary plate 35 may be rotated smoothly relative to the first spring-loaded latch 37 and the second spring-loaded latch 39. Preferably, a first half of the rotary plate 35 is semicircular in shape and a second half of the rotary plate 35 is semi-elliptical in shape, the second notch 35b and the third notch 35c are disposed at the interface of the first half and the second half, and the first notch 35a is disposed at the first half.

Figure 8:
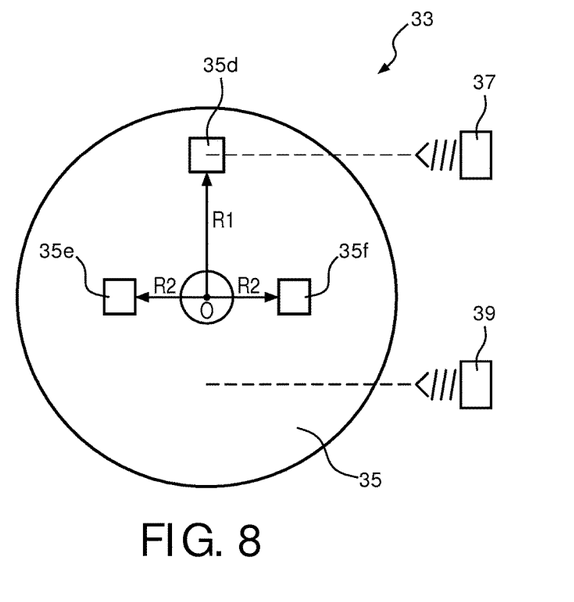
FIG. 8 is a schematic view showing a latching mechanism of a second embodiment of the present invention in which a rotary plate is locked in the first position.
Figure 8A:
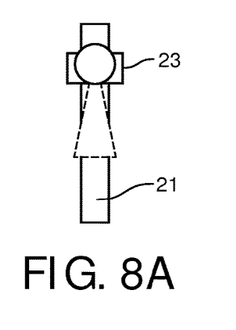
FIG. 8A shows an orientation of an x-ray tube assembly corresponding to FIG. 8.
Figure 9:
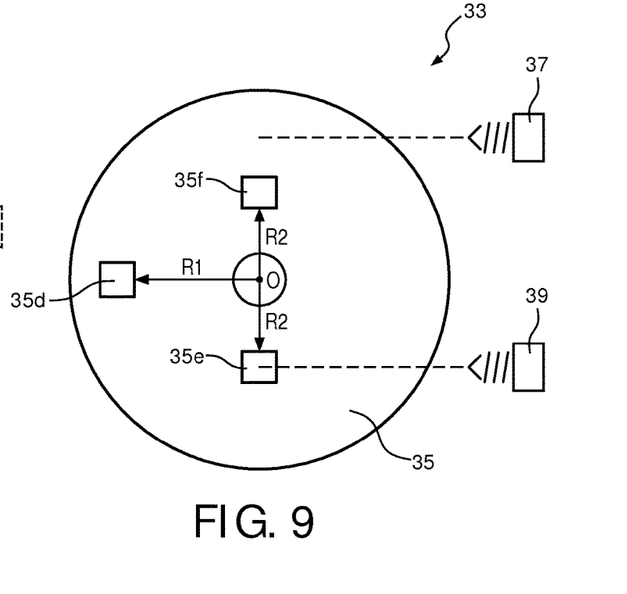
FIG. 9 is a schematic view showing a latching mechanism of a second embodiment of the present invention in which a rotary plate is locked in the second position.
Figure 9A:
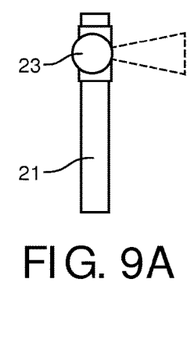
FIG. 9A shows an orientation of an x-ray tube assembly corresponding to FIG. 9.

FIG. 8 is a schematic view showing a latching mechanism of a second embodiment of the present invention in which a rotary plate is locked in the first position. FIG. 8A shows an orientation of an x-ray tube assembly corresponding to FIG. 8. FIG. 9 is a schematic view showing a latching mechanism of a second embodiment of the present invention in which a rotary plate is locked in the second position. FIG. 9A shows an orientation of an x-ray tube assembly corresponding to FIG. 9. As shown in FIGS. 8 and 9, the latching mechanism 33 of a second embodiment of the present invention comprises a rotary plate 35 to which the x-ray tube assembly 23 is mounted fixedly by means of a tube arm. The rotary plate 35 may be rotatably mounted to the supporting part so that the rotary plate 35 is rotatable about an axis relative to the supporting part. The axis passes through a point O on the rotary plate 35 perpendicularly to the rotary plate 35, also referred to as rotating axis. The rotary plate 35 comprises a first opening 35d, a second opening 35e and a third opening 35f which are disposed on the rotary plate 35. The second opening 35e and the third opening 35f are spaced from the first opening 35d by 90° about the rotating axis and from each other by 180° about the rotating axis. The distance from point O to the first opening 35d is R1, the distance from point O to the second opening 35e and the third opening 35f is R2, and R1≠R2.

The latching mechanism 33 further comprises a first spring-loaded latch 37 and a second spring-loaded latch 39 which are fixed on the supporting part. The first spring-loaded latch 37 and the second spring-loaded latch 39 are disposed diametrically, adjacent the rotary plate 35 and at a side of the rotary plate 35. The first spring-loaded latch 37 is configured to be pressed removably into the first opening 35d to lock the x-ray tube assembly 23 in the first position in which the x-ray is projected substantially vertically onto the region to be examined, as shown in FIG. 8A. The second spring-loaded latch 39 is configured to be pressed removably into the second opening 35e to lock the x-ray tube assembly 23 in the second position which is spaced from the first position by 90° in an anticlockwise direction when the rotary plate 35 is rotated by 90° about the rotating axis in the anticlockwise direction, as shown in FIG. 9. In the second position, the x-ray is projected substantially horizontally onto the region to be examined, as shown in FIG. 9A. Further, the second spring-loaded latch 39 is configured to be pressed removably into the third opening 35f to lock the x-ray tube assembly 23 in the third position which is spaced from the first position by 90° about the rotating axis in a clockwise direction when the rotary plate 35 is rotated by 90° about the rotating axis in the clockwise direction. In the third position, the x-ray is projected substantially horizontally onto the region to be examined in a direction opposite to the second direction.

Since R1≠R2, only the first spring-loaded latch 37 is pressed removably into the first opening 35d but the second spring-loaded latch 39 is not pressed into one of the second opening 35e and the third opening 35f when the x-ray tube assembly 23 is rotated to the first position, and only the second spring-loaded latch 39 is pressed removably into one of the second opening 35e and the third opening 35f, but the first spring-loaded latch 37 is not pressed into the first opening 35d, when the x-ray tube assembly 23 is rotated by 90° relative to the first position, as shown in FIGS. 8 and 9. In the second embodiment, the rotary plate 35 may be circular in shape.

Figure 10:
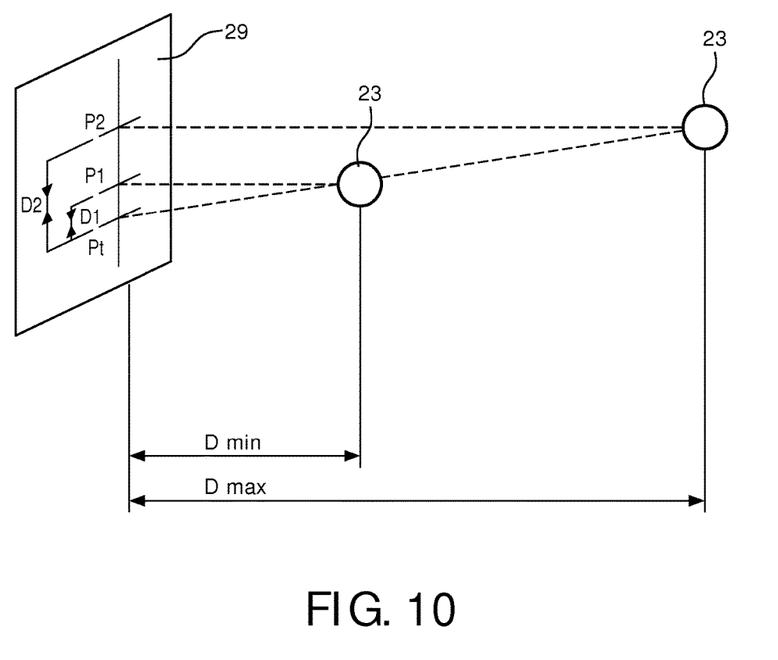
FIG. 10 is a schematic view showing a travel path of an x-ray tube assembly when aligning the second position of an x-ray tube assembly.

Alignments of the second position or the third position of the x-ray tube assembly 23 will be explained with reference to FIG. 10. FIG. 10 is a schematic view showing a travel path of an x-ray tube assembly when aligning the second position or third position of an x-ray tube assembly. Firstly, the center of alight beam projected onto the second detector 29 from an alignment light source within the x-ray tube assembly 23 is marked as position $P_1$ when the x-ray tube assembly 23 is moved together with the tube column 21 on a rail to a position where a distance D from the x-ray tube assembly 23 to the second detector 29 is a minimum distance. Then, the center of the light beam projected onto the second detector 29 from the alignment light source within the x-ray tube assembly 23 is marked as position $P_2$ when the x-ray tube assembly 23 is moved together with the tube column 21 on the rail to a position where a distance D from the x-ray tube assembly 23 to the second detector 29 is a maximum distance. It is desirable that position $P_1$ should demonstrate an overlap with position $P_2$. However, there is a deviation between position $P_1$ and position $P_2$ because of a stack up of various tolerances resulting from manufacture and/or installation of the x-ray imaging system. It is supposed that a target position after alignment is $P_t$. A distance $D_1$ between the target position $P_t$ and the position $P_1$ and a distance $D_2$ between the target position $P_t$ and the position $P_2$ should meet the equation:

$$D_1/D_2=D_{min}/D_{max}$$

The target position $P_t$ may be determined based on this equation and is marked on the second detector 29. Then, the position of the second spring-loaded latch 39 is fine-tuned so that the light from the alignment light source within the x-ray tube assembly 23 is projected onto the second detector 29 at the target position $P_t$, thereby accomplishing the alignments of the second position or the third position of the x-ray tube assembly 23.

The alignment of the first position of the x-ray tube assembly 23 is accomplished in a similar way by fine-tuning the position of the first spring-loaded latch 37. A detailed explanation of the alignment of the first position of the x-ray tube assembly 23 is omitted for conciseness.

According to the present invention, the alignment of the first position of the x-ray tube assembly 23 is accomplished by fine-tuning the position of the first spring-loaded latch 37, while the alignment of the second position and the third position of the x-ray tube assembly 23 are accomplished by fine-tuning the position of the second spring-loaded latch 39. The alignment of the first position latching and the second and third position latching are separate from each other. By virtue thereof, manufacturing tolerance control and installation of the x-ray imaging system are made much simpler and easier.

In the above-mentioned preferred embodiments, the rotary plate comprises three notches or three openings so that the x-ray is projected substantially horizontally onto the region to be examined whenever the x-ray tube assembly is rotated clockwise or anticlockwise by 90° about the rotating axis from the first position. However, it should be understood that it is feasible to have only one of the second notch and the third notch or the second opening and the third opening. In this case, the x-ray tube assembly is rotated from the first position by 90° about the rotating axis only in one direction.

Although the invention has been described in detail for the purpose of illustration based on what are currently considered to be the most practical and preferred embodiments, it is to be understood that such detail is solely for that purpose and that the invention is not limited to the disclosed embodiments, but on the contrary, is intended to cover modifications and equivalent arrangements that are within the spirit and scope of the appended claims.

The invention claimed is:

1. A latching mechanism for an x-ray tube assembly comprising:
    a rotary plate to which the x-ray tube assembly is fixedly mounted by means of a tube arm, the rotary plate being rotatably mounted to a supporting part to be rotatable about an axis relative to the supporting part, the axis passing through a point on the rotary plate perpendicularly to the rotary plate, the rotary plate comprising a first receiving portion and a second receiving portion, the second receiving portion being spaced from the first receiving portion by substantially 90° about the axis; and
    a first spring-loaded latch and a second spring-loaded latch which are fixed on the supporting part, the first spring-loaded latch (and the second spring-loaded latch being disposed diametrically and adjacent the rotary plate, the first spring-loaded latch being configured to be pressed removably into the first receiving portion to lock the x-ray tube assembly in a first position, the second spring-loaded latch being configured to be pressed removably into the second receiving portion to lock the x-ray tube assembly in a second position which is spaced from the first position by substantially 90° about the axis in a first direction.

2. The latching mechanism according to claim 1, wherein the rotary plate further comprises a third receiving portion spaced from the first receiving portion by substantially 90° and from the second receiving portion by substantially 180° about the axis, the second spring-loaded latch being configured to be pressed removably into the third receiving portion to lock the x-ray tube assembly in a third position which is spaced from the first position by substantially 90° about the axis in a second direction opposite to the first direction, a distance from the point to the first receiving portion is R1, a distance from the point to the second receiving portion and the third receiving portion is R2; and wherein R1≠R2 so that when the second spring-loaded latch is pressed removably into one of the second receiving portion and the third receiving portion, the first spring-loaded latch is not pressed into the other one of the second receiving portion and the third receiving portion.

3. The latching mechanism according to claim 2, wherein the first receiving portion, the second receiving portion and the third receiving portion are a first notch, a second notch and a third notch disposed on the periphery of the rotary plate, R1>R2, and the first spring-loaded latch and the second spring-loaded latch are disposed around the rotary plate.

4. The latching mechanism according to claim 3, wherein the difference between R1 and R2 is larger than a maximum distance over which the first spring-loaded latch can move after the first spring-loaded latch is removed out of the first notch so that only the second spring-loaded latch is pressed removably into one of the second notch and the third notch to lock the x-ray tube assembly in the second or third position, but the first spring-loaded latch is not pressed into the other one of the second notch and the third notch when the x-ray tube assembly is rotated by substantially 90° about the axis relative to the first position.

5. The latching mechanism according to claim 3, wherein except for the locations where the first notch, the second notch and the third notch are disposed, the rotary plate has an arc-shaped periphery so that the rotary plate is rotated smoothly relative to the first spring-loaded latch and the second spring-loaded latch.

6. The latching mechanism according to claim 3, wherein a first half of the rotary plate is semicircularin shape and a second half is semi-elliptical in shape, the second notch and the third notch are disposed at the interface of the first half and the second half, and the first notch is disposed at the first half.

7. The latching mechanism according to claim 2, wherein the first receiving portion, the second receiving portion and the third receiving portion area first opening, a second opening and a third opening disposed on the rotary plate, the first spring-loaded latch and the second spring-loaded latch are disposed at a side of the rotary plate.

8. The latching mechanism according to claim 7, wherein the rotary plate is circular in shape.

9. An x-ray imaging system comprising a latching mechanism according to claim 1.

10. The x-ray imaging system according to claim 9, wherein the x-ray imaging system comprises an x-ray tube assembly which is rotatably attached to a supporting part by means of a tube arm and the latching mechanism so that the x-ray tube assembly is capable of being rotated and then locked.

11. The x-ray imaging system according to claim 10, further comprising:
    a tube column configured to move back and forth on a rail, the supporting part being vertically slidably mounted onto the tube column so that the x-ray tube assembly is capable of moving vertically along the tube column;
    a first detector mounted below a patient table; and
    a second detector mounted on a wallstand.

12. The x-ray imaging system according to claim 10, wherein the first spring-loaded latch and the second spring-loaded latch are mounted on the supporting part.

13. The x-ray imaging system according to claim 10, wherein the x-ray tube assembly comprises an x-ray tube configured to generate and emit x-rays and a collimator configured to collimate the x-rays generated by the x-ray tube onto a region of a subject to be examined.

* * * * *